US006780164B2

(12) United States Patent
Bergheim et al.

(10) Patent No.: US 6,780,164 B2
(45) Date of Patent: Aug. 24, 2004

(54) L-SHAPED IMPLANT WITH BI-DIRECTIONAL FLOW

(75) Inventors: Olav B. Bergheim, Laguna Hills, CA (US); Morteza (Mory) Gharib, San Marino, CA (US)

(73) Assignee: Glaukos Corporation, Laguna Hills, CA (US)

( * ) Notice: Subject to any disclaimer, the term of this patent is extended or adjusted under 35 U.S.C. 154(b) by 0 days.

(21) Appl. No.: 10/395,627

(22) Filed: Mar. 21, 2003

(65) Prior Publication Data

US 2003/0191428 A1 Oct. 9, 2003

Related U.S. Application Data

(63) Continuation of application No. 09/549,350, filed on Apr. 14, 2000, now Pat. No. 6,638,239.

(51) Int. Cl.[7] ............................................... A61M 5/00
(52) U.S. Cl. .............................. 604/8; 604/27; 604/294
(58) Field of Search ................................. 604/9, 8, 294, 604/31, 33, 34, 521; 606/107, 166, 153

(56) References Cited

U.S. PATENT DOCUMENTS

| 3,788,327 A | 1/1974 | Donowitz et al. |
| 4,037,604 A | 7/1977 | Newkirk |
| 4,175,563 A | 11/1979 | Arenberg et al. |
| 4,402,681 A | 9/1983 | Haas et al. |
| 4,428,746 A | 1/1984 | Mendez |

(List continued on next page.)

FOREIGN PATENT DOCUMENTS

| AU | 200072059 A1 | 12/2000 |
| CA | 2244646 | 2/1999 |
| DE | 198 40 047 A 1 | 3/2000 |
| EP | 0 858 788 A1 | 8/1998 |
| EP | 0 898 947 A2 | 3/1999 |

(List continued on next page.)

OTHER PUBLICATIONS

Phillip C. Jacobi, M.D., Thomas S. Dietlein, M.D., and Gunter K. Krieglstein, M.D., *Goniocurettage for Removing Trabecular Meshwork: Clinical Results of a New Surgical Technique in Advanced Cronic Open–Angle Glaucoma*, American Journal of Ophthalmology, May 1999, pp. 505–510.

Phillip C. Jacobi, M.D., Thomas S. Dietlein, M.D., and Gunter K. Krieglstein, M.D., *Bimanual Trabecular Aspiration in Pseudoexfoliation Glaucoma*, Ophthalmology, 1998, No. 5, May 1998, pp. 886–894.

(List continued on next page.)

*Primary Examiner*—Edward K. Look
*Assistant Examiner*—Kimya N. McCoy
(74) *Attorney, Agent, or Firm*—Knobbe, Martens, Olson & Bear LLP

(57) ABSTRACT

Surgical methods and related medical devices for treating glaucoma are disclosed. The method comprises trabecular bypass surgery, which involve bypassing diseased trabecular meshwork with the use of a seton implant. The seton implant is used to prevent a healing process known as filling in, which has a tendency to close surgically created openings in the trabecular meshwork. The surgical method and novel implant are addressed to the trabecular meshwork, which is a major site of resistance to outflow in glaucoma. In addition to bypassing the diseased trabecular meshwork at the level of the trabecular meshwork, existing outflow pathways are also used or restored. The seton implant is positioned through the trabecular meshwork so that an inlet end of the seton implant is exposed to the anterior chamber of the eye and an outlet end is positioned into fluid collection channels at about an exterior surface of the trabecular meshwork or up to the level of aqueous veins.

6 Claims, 7 Drawing Sheets

U.S. PATENT DOCUMENTS

| | | |
|---|---|---|
| 4,501,274 A | 2/1985 | Skjaerpe |
| 4,521,210 A | 6/1985 | Wong |
| 4,554,918 A | 11/1985 | White |
| 4,604,087 A | 8/1986 | Joseph |
| 4,632,842 A | 12/1986 | Karwoski et al. |
| 4,634,418 A | 1/1987 | Binder |
| 4,718,907 A | 1/1988 | Karwoski et al. |
| 4,733,665 A | 3/1988 | Palmaz |
| 4,750,901 A | 6/1988 | Molteno |
| 4,787,885 A | 11/1988 | Binder |
| 4,804,382 A | 2/1989 | Turina et al. |
| 4,820,626 A | 4/1989 | Williams et al. |
| 4,846,172 A | 7/1989 | Berlin |
| 4,863,457 A | 9/1989 | Lee |
| 4,886,488 A | 12/1989 | White |
| 4,900,300 A | 2/1990 | Lee |
| 4,936,825 A | 6/1990 | Ungerleider |
| 4,946,436 A | 8/1990 | Smith |
| 4,968,296 A | 11/1990 | Ritch et al. |
| 5,041,081 A | 8/1991 | Odrich |
| 5,073,163 A | 12/1991 | Lippman |
| 5,092,837 A | 3/1992 | Ritch et al. |
| 5,095,887 A | 3/1992 | Leon et al. |
| 5,127,901 A | 7/1992 | Odrich |
| 5,129,895 A | 7/1992 | Vassiliadis et al. |
| 5,171,213 A | 12/1992 | Price, Jr. |
| 5,178,604 A | 1/1993 | Baerveldt et al. |
| 5,180,362 A | 1/1993 | Worst |
| 5,246,451 A | 9/1993 | Trescony et al. |
| 5,290,295 A | 3/1994 | Querals et al. |
| 5,300,020 A | 4/1994 | L'Esperance, Jr. |
| 5,318,513 A | 6/1994 | Leib et al. |
| 5,334,137 A | 8/1994 | Freeman |
| 5,338,291 A | 8/1994 | Speckman et al. |
| 5,346,464 A | 9/1994 | Camras |
| 5,360,399 A | 11/1994 | Stegmann |
| 5,370,607 A | 12/1994 | Memmen |
| 5,370,641 A | 12/1994 | O'Donnell, Jr. |
| 5,372,577 A | 12/1994 | Ungerleider |
| 5,397,300 A | 3/1995 | Baerveldt et al. |
| 5,433,701 A | 7/1995 | Rubinstein |
| 5,454,796 A | 10/1995 | Krupin |
| 5,476,445 A | 12/1995 | Baerveldt et al. |
| 5,486,165 A | 1/1996 | Stegmann |
| 5,516,522 A | 5/1996 | Peyman et al. |
| 5,520,631 A | 5/1996 | Nordquist et al. |
| 5,557,453 A | 9/1996 | Schalz et al. |
| 5,558,629 A | 9/1996 | Baerveldt et al. |
| 5,558,630 A | 9/1996 | Fisher |
| 5,562,641 A | 10/1996 | Flomenblit et al. |
| RE35,390 E | 12/1996 | Smith |
| 5,601,094 A | 2/1997 | Reiss |
| 5,601,549 A | 2/1997 | Miyagi |
| 5,626,558 A | 5/1997 | Suson |
| 5,626,559 A | 5/1997 | Solomon |
| 5,639,278 A | 6/1997 | Dereume et al. |
| 5,651,783 A | 7/1997 | Reynard |
| 5,665,114 A | 9/1997 | Weadock et al. |
| 5,670,161 A | 9/1997 | Healy et al. |
| 5,676,679 A | 10/1997 | Simon et al. |
| 5,681,275 A | 10/1997 | Ahmed |
| 5,702,414 A | 12/1997 | Richter et al. |
| 5,702,419 A | 12/1997 | Berry et al. |
| 5,704,907 A | 1/1998 | Nordquist et al. |
| 5,713,844 A | 2/1998 | Peyman |
| 5,723,005 A | 3/1998 | Herrick |
| 5,741,333 A | 4/1998 | Frid |
| 5,743,868 A | 4/1998 | Brown et al. |
| 5,752,928 A | 5/1998 | de Roulhac et al. |
| 5,766,243 A | 6/1998 | Christensen et al. |
| 5,785,674 A | 7/1998 | Mateen |
| 5,807,302 A | 9/1998 | Wandel |
| 5,810,870 A | 9/1998 | Myers et al. |
| 5,830,171 A | 11/1998 | Wallace |
| 5,836,939 A | 11/1998 | Negus et al. |
| 5,865,831 A | 2/1999 | Cozean et al. |
| 5,868,697 A | 2/1999 | Richter et al. |
| 5,879,319 A | 3/1999 | Pynson et al. |
| 5,882,327 A | 3/1999 | Jacob |
| 5,886,822 A | 3/1999 | Spitzer |
| 5,893,837 A | 4/1999 | Eagles et al. |
| 5,908,449 A | 6/1999 | Bruchman et al. |
| 5,932,299 A | 8/1999 | Katoot |
| 5,968,058 A | 10/1999 | Richter et al. |
| 5,981,598 A | 11/1999 | Tatton |
| 6,004,302 A | 12/1999 | Brierley |
| 6,007,510 A | 12/1999 | Nigam |
| 6,007,511 A | 12/1999 | Prywes |
| 6,033,434 A | 3/2000 | Borghi |
| 6,045,557 A | 4/2000 | White et al. |
| 6,050,970 A | 4/2000 | Baerveldt |
| 6,059,772 A | 5/2000 | Hsia et al. |
| 6,059,812 A | 5/2000 | Clerc et al. |
| 6,063,116 A | 5/2000 | Kelleher |
| 6,063,396 A | 5/2000 | Kelleher |
| 6,071,286 A | 6/2000 | Mawad |
| 6,077,299 A | 6/2000 | Adelberg et al. |
| 6,102,045 A | 8/2000 | Nordquist et al. |
| 6,142,990 A | 11/2000 | Burk |
| 6,165,210 A | 12/2000 | Lau et al. |
| 6,168,575 B1 | 1/2001 | Soltanpour |
| 6,174,305 B1 | 1/2001 | Mikus et al. |
| 6,193,656 B1 | 2/2001 | Jeffries et al. |
| 6,197,056 B1 | 3/2001 | Schachar |
| 6,203,513 B1 | 3/2001 | Yaron et al. |
| 6,228,873 B1 | 5/2001 | Brandt et al. |
| 6,231,597 B1 | 5/2001 | Deem et al. |
| 6,241,721 B1 | 6/2001 | Cozean et al. |
| 6,266,182 B1 | 7/2001 | Morita |
| 6,268,398 B1 | 7/2001 | Ghosh et al. |
| 6,342,058 B1 | 1/2002 | Portney |
| 6,375,642 B1 | 4/2002 | Grieshaber et al. |
| 6,450,984 B1 | 9/2002 | Lynch et al. |
| 6,464,724 B1 | 10/2002 | Lynch et al. |
| 6,544,249 B1 | 4/2003 | Yu et al. |
| 2002/0026200 A1 | 2/2002 | Savage |
| 2002/0099434 A1 | 7/2002 | Buscemi et al. |

FOREIGN PATENT DOCUMENTS

| | | |
|---|---|---|
| EP | 1 114 627 A1 | 11/2000 |
| FR | 93 11476 | 3/1995 |
| GB | 2296633 A | 7/1996 |
| JP | 11-123205 | 11/1999 |
| WO | WO 89/00869 | 2/1989 |
| WO | WO 91/18568 | 12/1991 |
| WO | WO 92/19294 | 11/1992 |
| WO | WO 94/13234 | 6/1994 |
| WO | WO 94/21205 | 9/1994 |
| WO | WO 95/08310 | 3/1995 |
| WO | WO 98/30181 | 1/1998 |
| WO | WO 98/35639 | 8/1998 |
| WO | WO 99/26567 | 6/1999 |
| WO | WO 99/30641 | 6/1999 |
| WO | WO 99/38470 | 8/1999 |
| WO | WO 00/13627 | 3/2000 |
| WO | WO 00/64389 | 4/2000 |
| WO | WO 00/64390 | 4/2000 |
| WO | WO 00/64391 | 4/2000 |
| WO | WO 00/64393 | 11/2000 |
| WO | WO 00/72788 A1 | 12/2000 |
| WO | WO 01/50943 | 7/2001 |

| | | |
|---|---|---|
| WO | WO 01/78631 A2 | 10/2001 |
| WO | WO 01/78656 A2 | 10/2001 |
| WO | WO 03/015659 A2 | 2/2003 |

OTHER PUBLICATIONS

Arthur L. Schwartz, M.D., and Douglas R. Anderson, M.D., *Trabecular Surgery, Arch Ophthalmol.*, vol. 92, Aug. 1974, pp. 134–138.

R. A. Hill, Q. Ren, D. C. Nguyen, L–H. Liaw, and M. W. Berns, *Free–electron Laser (FEL) Ablation of Ocular Tissues, Laser Med Sci* 1998, pp. 13:219–226.

Maurice H. Luntz, M.D., and D. G. Livingston, B.SC., *Trabeculotomy AB Externo and Trabeculectomy in Cogenital and Adult–Onset Glaucoma, American Journal of Ophthalmology*, vol. 83, No. 2, Feb. 1997, pp. 174–179.

W. M. Grant, M.D., *Further Studies on Facility of Flow Through the Trabecular Meshwork, A.M.A. Archives of Ophthalmology*, vol. 60, Oct. 1958, pp. 523–533.

Richard A. Hill, M.D., George Baerveldt, M.D., Serdar A. Ozler, M.D., Michael Pickford, B.A., Glen A. Profeta, B.S., and Michael W. Berns, Ph.D., *Lawser Trabecular Ablation (LTA), Laser in Surgery and Medicine*, vol. 11, 1991, pp. 341–346.

Detlev Spiegel, M.D., Karin Kobuch, M.D., Richard A. Hill, M.D., Ronald L. Gross, M.D., *Schlemm's Canal Implant: A New Method to Lower Intraocular Pressure in Patients with POAG, Ophthalmic Surgery and Lasers*, vol. 30, No. 6, Jun. 1999, pp. 492–494.

Copending U.S. patent application of Dr. Richard Hill, Ser. No. 09/549,349, filed on Apr. 14, 2000, entitled *Device for Glaucoma Treatment and Methods Thereof*.

L. Jay Katz, M.D., *A Call for Innovative Operations for Glaucoma, Arch Ophthalmology*, vol. 118, Mar. 2000, pp. 412–413.

Anselm Kampik and Franz Grehn, *Nutzen und Risiken Augenärzticher Therapie, Hauptreferate det XXXIII, Essener Fortbildung für Augenärzte*, Dec. 1998. (English translated version entitled Benefits and Risks of Ophthalmological Therapy.)

Detlev Spiegel, 7 *Chirurgische Glaukomtherapie*, pp. 79–88.

U.S. patent application Ser. No. 09/452,963, filed Dec. 2, 1999, entitled: *Expandable/Retractable Stent For Venous And Valvular Annulus Use*.

Grieshaber, et al., *Method and Device to Improve Aqueous Humor Drainage in an Eye*, Jan. 1, 2002, Pub. No. US 2002/0013546 A1.

Hans Hoerauf, Christopher Wirbelauer, Christian Scholz, Ralf Engelhardt, Peter Koch, Horst Laqua, and Reginald Birngruber, *Slit–Lamp–Adapted Optical Coherence Tomography of the Anterior Segment, Graefe's Arch Clin. Exp. Ophthalmol*, vol. 238, May 1999, pp. 8–18.

Sumita Radhakrishnam, Andrew M. Rollins, Jonathan E. Roth, S. Yazdanfar, Volker Westphal, David Bardenstein and Joseph Izatt, *Real–time Optical Coherence Tomography of the Anterior Segment at 1310 NM, Arch Ophthalmology*, vol. 119, Aug. 2001, pp. 1179–1185.

I. Grierson, R. C. Howes and Q. Wang, *Age–related Changes in the Canal of Schlemm, Exp. Eye Res.*, vol. 39, 1985, pp. 505–512.

Luanna K. Putney, Cecile Rose T. Vibat, and Martha E. O'Donnell, *Intracellular C1 Regulates Na–K–C1 Cotransport Activity in Human Trabecular Meshwork Cells, 1999 American Physiological Society*, Sep. 1999, pp. C–373 through C–383.

Edited by Kevin Strange, *Cellular and Molecular Physiology of Cell Volume Regulation, Library of Congress Cataloging in–Publication Data*, CRC Press, Inc., pp. 312–321.

William Tatton, Ruth M. E. Chalmers–Redman, Ajay Sud, Steven M. Podos, and Thomas Mittag, *Maintaining Mitochondrial Membrane Impermeability: An Opportunity for New Therapy in Glaucoma?, Survey of Ophthalmology*, vol. 45, Supp. 3, May 2001, pp. S–277 through S–283.

Robert W. Nickells, *Apoptosis of Retinal Ganglion Cells in Glaucoma: An Update of the Molecular Pathways Involved in Cell Death, Survey of Ophthalmology*, vol. 43, Supp. 1, Jun. 1999, pp. S–151 through S–161.

Grune & Stratton, Harcourt Brace Jovanovich Publishers, edited by J. E. Cairns, *Glaucoma*, vol. 1, Chap. 14, *Anatomy of the Aqueous Outflow Channels*, by Johannes W. Rohen, pp. 277–296.

Yasuhiro Matsumoto and Douglas H. Johnson, *Trabecular Meshwork Phagocytosis in Glaucomatous Eyes, Ophthalmologica 1977*, vol. 211, pp. 147–152.

M. Bruce Shields, M.D., *A Study Guide for Glaucoma: Aqueous Humor Dynamics*, Copyright 1982, pp. 6–43.

M. A. Johnstone, R. Stegmann and B. A. Smit, *American Glaucoma Society, $12^{th}$ Annual Meeting, Cylindrical Tubular Structures Spanning from Trabecular Meshwork Across SC:* Laboratory Studies with SEM, TEM & Tracers Correlated with Clinical Findings, p. 39.

W. G. Tatton, *Apoptotic Mechanisms in Neurodegeneration: Possible Relevance to Glaucoma, European Journal of Ophthalmology*, vol. 9, Supp. 1, Jan.–Mar. 1999, pp. S–22 through S–29.

L-SHAPED IMPLANT WITH BI-DIRECTIONAL FLOW

CLAIM OF PRIORITY AND RELATED APPLICATIONS

This patent application is a continuation application of U.S. patent application Ser. No. 09/549,350, filed Apr. 14, 2000, now U.S. Pat. No 6,638,239 which is incorporated in its entirety by reference herein. This application is also related to U.S. patent application Ser. No. 10/309,711, filed Dec. 4, 2002, U.S. patent application Ser. No. 10/395,633, filed Mar. 21, 2003, U.S. patent application Ser. No. 10/395,631, filed Mar. 21, 2003, and U.S. patent application Ser. No. 10/395,472, filed Mar. 21, 2003, all of which are incorporated in their entirety by reference herein.

FIELD OF THE INVENTION

The present invention generally relates to improved medical devices and methods for the reduction of elevated pressure in organs of the human body. More particularly, the present invention relates to the treatment of glaucoma by trabecular bypass surgery, which is a means for using an implant or seton, such as a micro stent, shunt or the like, to bypass diseased trabecular meshwork at the level of trabecular meshwork and use/restore existing outflow pathways.

BACKGROUND OF THE INVENTION

About two percent of people in the United States have glaucoma. Glaucoma is a group of eye diseases that causes pathological changes in the optic disk and corresponding visual field loss resulting in blindness if untreated. Intraocular pressure elevation is the major etiologic factor in all glaucomas.

In glaucomas associated with an elevation in eye pressure the source of resistance to outflow is in the trabecular meshwork. The tissue of the trabecular meshwork allows the "aqueous" to enter Schlemm's canal, which then empties into aqueous collector channels in the posterior wall of Schlemm's canal and then into aqueous veins. The aqueous or aqueous humor is a transparent liquid that fills the region between the cornea at the front of the eye and the lens. The aqueous humor is constantly secreted by the ciliary body around the lens, so there is a continuous flow of the aqueous humor from the ciliary body to the eye's front chamber. The eye's pressure is determined by a balance between the production of aqueous and its exit through the trabecular meshwork (major route) or via uveal scleral outflow (minor route). The trabecular meshwork is located between the outer rim of the iris and the internal periphery of the cornea. The portion of the trabecular meshwork adjacent to Schlemm's canal causes most of the resistance to aqueous outflow (juxtacanilicular meshwork).

Glaucoma is grossly classified into two categories: closed-angle glaucoma and open-angle glaucoma. The closed-angle glaucoma is caused by closure of the anterior angle by contact between the iris and the inner surface of the trabecular meshwork. Closure of this anatomical angle prevents normal drainage of aqueous humor from the anterior chamber of the eye. Open-angle glaucoma is any glaucoma in which the angle of the anterior chamber remains open, but the exit of aqueous through the trabecular meshwork is diminished. The exact cause for diminished filtration is unknown for most cases of open-angle glaucoma. However, there are secondary open-angle glaucomas which may include edema or swelling of the trabecular spaces (from steroid use), abnormal pigment dispersion, or diseases such as hyperthyroidism that produce vascular congestion.

All current therapies for glaucoma are directed at decreasing intraocular pressure. This is initially by medical therapy with drops or pills that reduce the production of aqueous humor or increase the outflow of aqueous. However, these various drug therapies for glaucoma are sometimes associated with significant side effects, such as headache, blurred vision, allergic reactions, death from cardiopulmonary complications and potential interactions with other drugs. When the drug therapy fails, surgical therapy is used. Surgical therapy for open-angle glaucoma consists of laser (trabeculoplasty), trabeculectomy and aqueous shunting implants after failure of trabeculectomy or if trabeculectomy is unlikely to succeed. Trabeculectomy is a major surgery which is most widely used and is augmented with topically applied anticancer drugs such as 5-flurouracil or mitomycin-c to decrease scarring and increase surgical success.

Approximately 100,000 trabeculectomies are performed on Medicare age patients per year in the United States. This number would increase if the morbidity associated with trabeculectomy could be decreased. The current morbidity associated with trabeculectomy consists of failure (10–15%), infection (a life long risk about 2–5%), choroidal hemorrhage (1%, a severe internal hemorrhage from pressure too low resulting in visual loss), cataract formation, and hypotony maculopathy (potentially reversible visual loss from pressure too low).

If it were possible to bypass the local resistance to outflow of aqueous at the point of the resistance and use existing outflow mechanisms, surgical morbidity would greatly decrease. The reason for this is that the episcleral aqueous veins have a backpressure that would prevent the eye pressure from going too low. This would virtually eliminate the risk of hypotony maculopathy and choroidal hemorrhage. Furthermore, visual recovery would be very rapid and risk of infection would be very small (a reduction from 2–5% to 0.05%). Because of these reasons surgeons have tried for decades to develop a workable surgery for the trabecular meshwork.

The previous techniques, which have been tried, are goniotomy/trabeculotomy, and other mechanical disruption of the trabecular meshwork, such as trabeculopuncture, goniophotoablation, laser trabecular ablation and goniocurretage. They are briefly described below.

Goniotomy/Trabeculotomy: Goniotomy and trabeculotomy are simple and directed techniques of microsurgical dissection with mechanical disruption of the trabecular meshwork. These initially had early favorable responses in the treatment of open-angle glaucoma. However, long-term review of surgical results showed only limited success in adults. In retrospect, these procedures probably failed secondary to repair mechanisms and a process of "filling in". The filling in is the result of a healing process which has the detrimental effect of collapsing and closing in of the created opening throughout the trabecular meshwork. Once the created openings close, the pressure builds back up and the surgery fails.

Trabeculopuncture: Q-switched Neodymiun (Nd):YAG lasers also have been investigated as an optically invasive technique for creating full-thickness holes in trabecular meshwork. However, the relatively small hole created by this trabeculopuncture technique exhibits a filling in effect and fails.

Goniophotoablation/Laser Trabecular Ablation: Goniophotoablation is disclosed by Berlin in U.S. Pat. No. 4,846, 172, and describes the use of an excimer laser to treat glaucoma by ablating the trabecular meshwork. This was not demonstrated by clinical trial to succeed. Hill et al. used an Erbium:YAG laser to create full thickness holes through trabecular meshwork (Hill et al., Lasers in Surgery and Medicine 11:341–346, 1991). This technique was investigated in a primate model and a limited human clinical trial at the University of California, Irvine. Although morbidity was zero in both trials, success rates did not warrant further human trials. Failure again was from filling in of created defects in trabecular meshwork by repair mechanisms. Neither of these is a valid surgical technique for the treatment of glaucoma.

Goniocurretage: This is an ab-interno (from the inside) mechanical disruptive technique. This uses an instrument similar to a cyclodialysis spatula with a microcurrette at the tip. Initial results are similar to trabeculotomy that fails secondary to repair mechanisms and a process of filling in.

Although trabeculectomy is the most commonly performed filtering surgery, Viscocanulostomy (VC) and non-penetrating trabeculectomy (NPT) are two new variations of filtering surgery. These are ab-externo (from the outside), major ocular procedures in which Schlemm's canal is surgically exposed by making a large and very deep scleral flap. In the VC procedure, Schlemm's canal is canulated and viscoelastic substance injected (which dilates Schlemm's canal and the aqueous collector channels). In the NPT procedure, the inner wall of Schlemm's canal is stripped off after surgically exposing the canal.

Trabeculectomy, VC, and NPT are performed under a conjunctival and scleral flap, such that the aqueous humor is drained onto the surface of the eye or into the tissues located within the lateral wall of the eye. Normal physiological outflows are not used. These surgical operations are major procedures with significant ocular morbidity. When Trabeculectomy, VC, and NPT are thought to have a low chance for success, a number of implantable drainage devices have been used to ensure that the desired filtration and outflow of aqueous humor through the surgical opening will continue. The risk of placing a glaucoma drainage implant also includes hemorrhage, infection and postoperative double vision that is a complication unique to drainage implants.

Examples of implantable shunts or devices for maintaining an opening for the release of aqueous humor from the anterior chamber of the eye to the sclera or space underneath conjunctiva have been disclosed in U.S. Pat. No. 6,007,511 (Prywes), Pat. No. 6,007,510 (Nigam), Pat. No. 5,893,837 (Eagles et al.), Pat. No. 5,882,327 (Jacob), Pat. No. 5,879, 319 (Pynson et al.), Pat. No. 5,807,302 (Wandel), Pat. No. 5,752,928 (de Roulhac et al.), Pat. No. 5,743,868 (Brown et al.), Pat. No. 5,704,907 (Nordquist et al.), Pat. No. 5,626,559 (Solomon), Pat. No. 5,626,558 (Suson), Pat. No. 5,601,094 (Reiss), U.S. Pat. No. RE. 35,390 (Smith), Pat. No. 5,558, 630 (Fisher), Pat. No. 5,558,629 (Baerveldt et al.), Pat. No. 5,520,631 (Nordquist et al.), Pat. No. 5,476,445 (Baerveldt et al.), Pat. No. 5,454,796 (Krupin), Pat. No. 5,433,701 (Rubinstein), Pat. No. 5,397,300 (Baerveldt et al.), Pat. No. 5,372,577 (Ungerleider), Pat. No. 5,370,607 (Memmen), Pat. No. 5,338,291 (Speckman et al.), Pat. No. 5,300,020 (L'Esperance, Jr.), Pat. No. 5,178,604 (Baerveldt et al.), Pat. No. 5,171,213 (Price, Jr.), Pat. No. 5,041,081 (Odrich), Pat. No. 4,968,296 (Ritch et al.), Pat. No. 4,936,825 (Ungerleider), Pat. No. 4,886,488 (White), Pat. No. 4,750, 901 (Molteno), Pat. No. 4,634,418 (Binder), Pat. No. 4,604, 087 (Joseph), Pat. No. 4,554,918 (White), Pat. No. 4,521, 210 (Wong), Pat. No. 4,428,746 (Mendez), Pat. No. 4,402, 681 (Haas et al.), Pat. No. 4,175,563 (Arenberg et al.), and Pat. No. 4,037,604 (Newkirk).

All of the above embodiments and variations thereof have numerous disadvantages and moderate success rates. They involve substantial trauma to the eye and require great surgical skill by creating a hole over the full thickness of the sclera/cornea into the subconjunctival space. Furthermore, normal physiological outflow pathways are not used. The procedures are mostly performed in an operating room generating a facility fee, anesthesiologist's professional fee and have a prolonged recovery time for vision. The complications of filtration surgery have inspired ophthalmic surgeons to look at other approaches to lowering intraocular pressure.

The trabecular meshwork and juxtacanilicular tissue together provide the majority of resistance to the outflow of aqueous and, as such, are logical targets for surgical removal in the treatment of open-angle glaucoma. In addition, minimal amounts of tissue are altered and existing physiologic outflow pathways are utilized. Trabecular bypass surgery has the potential for much lower risks of choroidal hemorrhage, infection and uses existing physiologic outflow mechanisms. This surgery could be performed under topical anesthesia in a physician's office with rapid visual recovery.

Therefore, there is a great clinical need for the treatment of glaucoma by a method that would be faster, safer and less expensive than currently available modalities. Trabecular bypass surgery is an innovative surgery which uses a micro stent, shunt, or other implant to bypass diseased trabecular meshwork alone at the level of trabecular meshwork and use or restore existing outflow pathways. The object of the present invention is to provide a means and methods for treating elevated intraocular pressure in a manner which is simple, effective, disease site specific and can be performed on an outpatient basis.

SUMMARY OF THE INVENTION

In some preferred embodiments, the seton has an inlet portion configured to extend through a portion of the trabecular meshwork of an eye, and an outlet portion configured to extend into Schlemm's canal of the eye, wherein the inlet portion is disposed at an angle relative to the outlet portion. In some embodiments, the outlet portion has a lumen with an oval cross-section having a long axis.

The outlet portion in certain embodiments has a longitudinal axis, such that the long axis of the oval cross-section and the longitudinal axis of the outlet portion define a plane, the inlet portion having a longitudinal axis which lies outside the plane at an angle $\theta$ (theta) thereto.

In some preferred arrangements, the seton comprises an inlet portion, configured to extend through a portion of the trabecular meshwork; an outlet portion, configured to extend into Schlemm's canal; and at least one protrusion on the outlet portion, configured to exert traction against an inner surface of Schlemm's canal. This protrusion can comprise at least one barb or ridge.

Some preferred embodiments comprise an inlet portion configured to extend through a portion of the trabecular meshwork, an outlet portion configured to extend into Schlemm's canal, and a one-way valve within the inlet and/or outlet portions.

A method for delivering a seton within an eye is disclosed, comprising providing an elongate guide member, advancing a distal end of the guide member through at least a portion of the trabecular meshwork of the eye, advancing the seton along the guide member toward the distal end, and positioning the seton to conduct aqueous humor between the anterior chamber of the eye and Schlemm's canal.

In certain embodiments, the advancing of the guide member comprises advancing it from the anterior chamber into the trabecular meshwork. In further embodiments, the positioning comprises positioning an end of the seton within Schlemm's canal adjacent to an aqueous collection channel.

Certain preferred embodiments include an apparatus for delivering a seton to the anterior chamber of an eye comprising an elongate tube having a lumen, an outer surface, and a distal end; a removable, elongate guide member within the lumen, configured to permit the seton to be advanced and to be positioned in the trabecular meshwork of the eye. This apparatus can further comprise a cutting member positioned at the distal end of the tube. The cutting member can be selected from the group consisting of a knife, a laser probe, a pointed guide member, a sharpened distal end of said tube, and an ultrasonic cutter. The apparatus can also further comprise an opening in the outer surface of the tube, configured to allow fluid infusion into the eye.

In further preferred embodiments, an apparatus for delivering a seton in an eye, comprises an elongate member adapted for insertion into an anterior chamber of the eye, the elongate member having a distal end portion configured to retain the seton therein, the distal end portion comprising a cutting member configured to form an opening in the trabecular meshwork of the eye for receipt of the seton, such that one end of the seton is in Schlemm's canal. The elongate member can further comprise a lumen which conducts fluid toward said distal end portion.

The preferred embodiment provides further surgical treatment of glaucoma (trabecular bypass surgery) at the level of trabecular meshwork and restores existing physiological outflow pathways. An implant bypasses diseased trabecular meshwork at the level of trabecular meshwork and which restores existing physiological outflow pathways. The implant has an inlet end, an outlet end and a lumen therebetween. The inlet is positioned in the anterior chamber at the level of the internal trabecular meshwork and the outlet end is positioned at about the exterior surface of the diseased trabecular meshwork and/or into fluid collection channels of the existing outflow pathways.

In accordance with a preferred method, trabecular bypass surgery creates an opening or a hole through the diseased trabecular meshwork through minor microsurgery. To prevent "filling in" of the hole, a biocompatible elongated implant is placed within the hole as a seton, which may include, for example, a solid rod or hollow tube. In one exemplary embodiment, the seton implant may be positioned across the diseased trabecular meshwork alone and it does not extend into the eye wall or sclera. In another embodiment, the inlet end of the implant is exposed to the anterior chamber of the eye while the outlet end is positioned at the exterior surface of the trabecular meshwork. In another exemplary embodiment, the outlet end is positioned at and over the exterior surface of the trabecular meshwork and into the fluid collection channels of the existing outflow pathways. In still another embodiment, the outlet end is positioned in the Schlemm's canal. In an alternative embodiment, the outlet end enters into fluid collection channels up to the level of the aqueous veins with the seton inserted in a retrograde or antegrade fashion.

According to the preferred embodiment, the seton implant is made of biocompatible material, which is either hollow to allow the flow of aqueous humor or solid biocompatible material that imbibes aqueous. The material for the seton may be selected from the group consisting of porous material, semi-rigid material, soft material, hydrophilic material, hydrophobic material, hydrogel, elastic material, and the like.

In further accordance with the preferred embodiment, the seton implant may be rigid or it may be made of relatively soft material and is somewhat curved at its distal section to fit into the existing physiological outflow pathways, such as Schlemm's canal. The distal section inside the outflow pathways may have an oval shape to stabilize the seton in place without undue suturing. Stabilization or retention of the seton may be further strengthened by a taper end and/or by at least one ridge or rib on the exterior surface of the distal section of the seton, or other surface alterations designed to retain the seton.

In one embodiment, the seton may include a micropump, one way valve, or semi-permeable membrane if reflux of red blood cells or serum protein becomes a clinical problem. It may also be useful to use a biocompatible material that hydrates and expands after implantation so that the seton is locked into position around the trabecular meshwork opening or around the distal section of the seton.

One of the advantages of trabecular bypass surgery, as disclosed herein, and the use of a seton implant to bypass diseased trabecular meshwork at the level of trabecular meshwork and thereby use existing outflow pathways is that the treatment of glaucoma is substantially simpler than in existing therapies. A further advantage of the invention is the utilization of simple microsurgery that may be performed on an outpatient basis with rapid visual recovery and greatly decreased morbidity. Finally, a distinctly different approach is used than is found in existing implants. Physiological outflow mechanisms are used or re-established by the implant of the present invention, in contradistinction with previously disclosed methodologies.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF THE PREFERRED EMBODIMENT

Referring to FIGS. 1 to 7, what is shown is a method for the treatment of glaucoma by trabecular bypass surgery. In particular, a seton implant is used to bypass diseased trabecular meshwork at the level of trabecular meshwork to use or restore existing outflow pathways and methods thereof.

Figure 1:
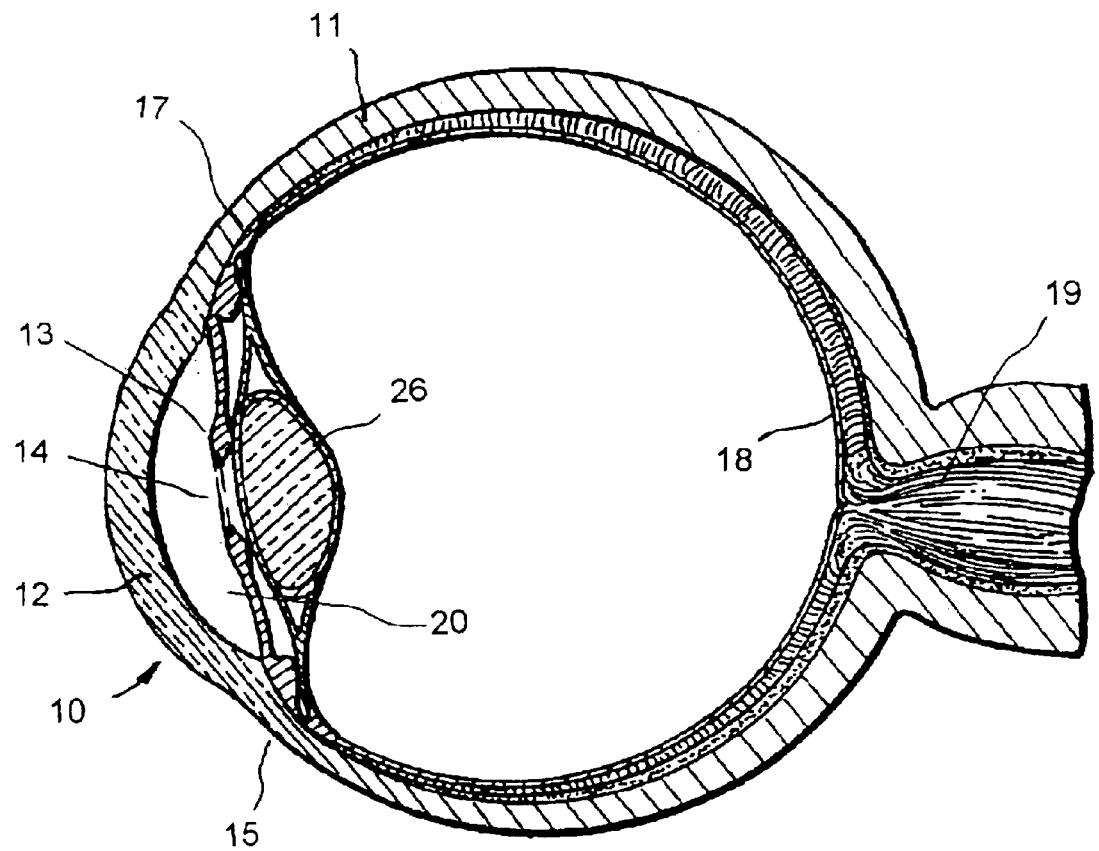
FIG. 1 is a sectional view of an eye for illustration purposes.
Figure 2:
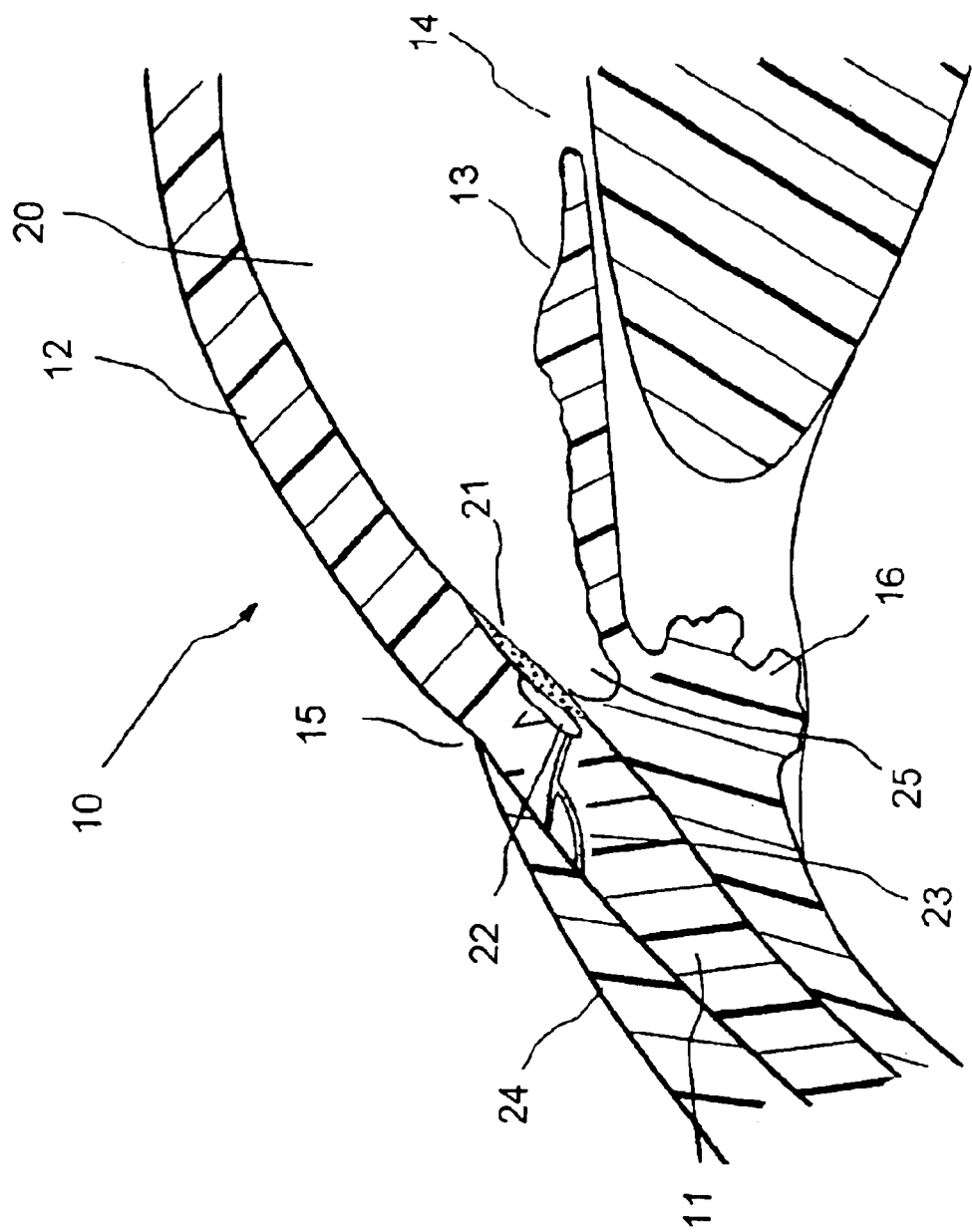
FIG. 2 is a close-up sectional view, showing the anatomical diagram of trabecular meshwork and the anterior chamber of the eye.

For background illustration purposes, FIG. 1 shows a sectional view of an eye 10, while FIG. 2 shows a close-up view, showing the relative anatomical locations of the trabecular meshwork, the anterior chamber, and Schlemm's canal. Thick collagenous tissue known as sclera 11 covers the entire eye 10 except that portion covered by the cornea 12. The cornea 12 is a thin transparent tissue that focuses and transmits light into the eye and the pupil 14 which is the circular hole in the center of the iris 13 (colored portion of the eye). The cornea 12 merges into the sclera 11 at a juncture referred to as the limbus 15. The ciliary body 16 begins internally in the eye and extends along the interior of the sclera 11 and becomes the choroid 17. The choroid 17 is a vascular layer of the eye underlying retina 18. The optic nerve 19 transmits visual information to the brain and is sequentially destroyed by glaucoma.

The anterior chamber 20 of the eye 10, which is bound anteriorly by the cornea 12 and posteriorly by the iris 13 and lens 26, is filled with aqueous. Aqueous is produced primarily by the ciliary body 16 and reaches the anterior chamber angle 25 formed between the iris 13 and the cornea 12 through the pupil 14. In a normal eye, the aqueous is removed through the trabecular meshwork 21. Aqueous passes through trabecular meshwork 21 into Schlemm's canal 22 and through the aqueous veins 23 which merge with blood-carrying veins and into venous circulation. Intraocular pressure of the eye 10 is maintained by the intricate balance of secretion and outflow of the aqueous in the manner described above. Glaucoma is characterized by the excessive buildup of aqueous fluid in the anterior chamber 20 which produces an increase in intraocular pressure (fluids are relatively incompressible and pressure is directed equally to all areas of the eye).

Figure 5:
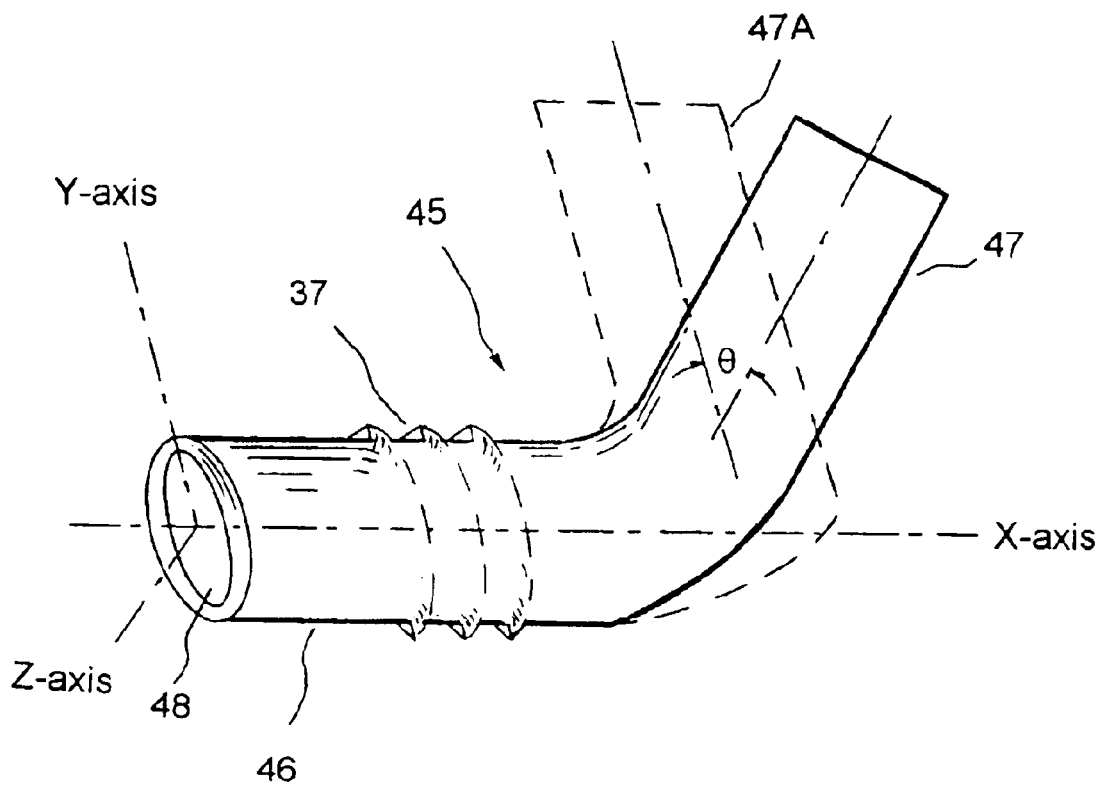
FIG. 5 is another embodiment of the seton implant constructed in accordance with the principles of the invention.

As shown in FIG. 2, the trabecular meshwork 21 constitutes a small portion of the sclera 11. It is understandable that creating a hole or opening for implanting a device through the tissues of the conjunctiva 24 and sclera 11 is relatively a major surgery as compared to a surgery for implanting a device through the trabecular meshwork 21 only. A seton implant 31 of the present invention for either using or restoring existing outflow pathways positioned through the trabecular meshwork 21 is illustrated in FIG. 5.

In a first embodiment, a method for increasing aqueous humor outflow in an eye of a patient to reduce the intraocular pressure therein. The method comprises bypassing diseased trabecular meshwork at the level of the trabecular meshwork and thereby restoring existing outflow pathways. Alternately, a method for increasing aqueous humor outflow in an eye of a patient to reduce an intraocular pressure therein is disclosed. The method comprises bypassing diseased trabecular meshwork at a level of said trabecular meshwork with a seton implant and using existing outflow pathways. The seton implant 31 may be an elongated seton or other appropriate shape, size or configuration. In one embodiment of an elongated seton implant, the seton has an inlet end, an outlet end and a lumen therebetween, wherein the inlet end is positioned at an anterior chamber of the eye and the outlet end is positioned at about an exterior surface of said diseased trabecular meshwork. Furthermore, the outlet end may be positioned into fluid collection channels of the existing outflow pathways. Optionally, the existing outflow pathways may comprise Schlemm's canal 22. The outlet end may be further positioned into fluid collection channels up to the level of the aqueous veins with the seton inserted either in a retrograde or antegrade fashion with respect to the existing outflow pathways.

In a further alternate embodiment, a method is disclosed for increasing aqueous humor outflow in an eye of a patient to reduce an intraocular pressure therein. The method comprises (a) creating an opening in trabecular meshwork, wherein the trabecular meshwork comprises an interior side and exterior side; (b) inserting a seton implant into the opening; and (c) transporting the aqueous humor by said seton implant to bypass the trabecular meshwork at the level of said trabecular meshwork from the interior side to the exterior side of the trabecular meshwork.

Figure 3:
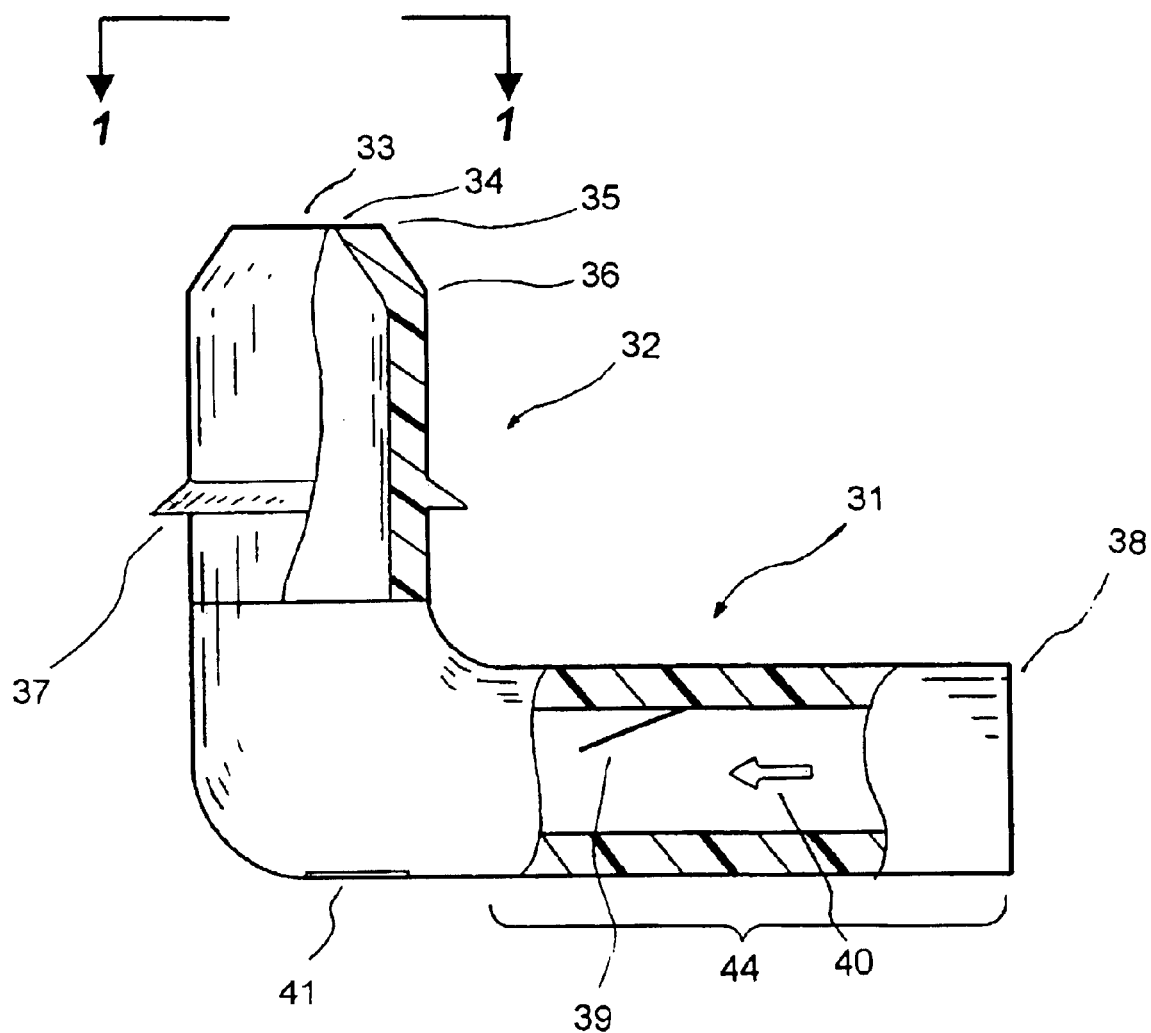
FIG. 3 is an embodiment of the seton implant constructed according to the principles of the invention.

FIG. 3 shows an embodiment of the seton implant 31 constructed according to the principles of the invention. The seton implant may comprise a biocompatible material, such as a medical grade silicone, for example, the material sold under the trademark Silastic™, which is available from Dow Corning Corporation of Midland, Mich., or polyurethane, which is sold under the trademark Pellethane™, which is also available from Dow Corning Corporation. In an alternate embodiment, other biocompatible materials (biomaterials) may be used, such as polyvinyl alcohol, polyvinyl pyrolidone, collagen, heparinized collagen, tetrafluoroethylene, fluorinated polymer, fluorinated elastomer, flexible fused silica, polyolefin, polyester, polysilison, mixture of biocompatible materials, and the like. In a further alternate embodiment, a composite biocompatible material by surface coating the above-mentioned biomaterial may be used, wherein the coating material may be selected from the group consisting of polytetrafluoroethylene (PTFE), polyimide, hydrogel, heparin, therapeutic drugs, and the like.

The main purpose of the seton implant is to assist in facilitating the outflow of aqueous in an outward direction 40 into the Schlemm's canal and subsequently into the aqueous collectors and the aqueous veins so that the intraocular pressure is balanced. In one embodiment, the seton implant 31 comprises an elongated tubular element having a distal section 32 and an inlet section 44. A rigid or flexible distal section 32 is positioned inside one of the existing outflow pathways. The distal section may have either a tapered outlet end 33 or have at least one ridge 37 or other retention device protruding radially outwardly for stabilizing the seton implant inside said existing outflow pathways after implantation. For stabilization purposes, the outer surface of the distal section 32 may comprise a stubbed surface, a ribbed surface, a surface with pillars, a textured surface, or the like. The outer surface 36, including the outer region 35 and inner region 34 at the outlet end 33, of the seton implant is biocompatible and tissue compatible so that the interaction/irritation between the outer surface and the surrounding tissue is minimized. The seton implant may comprise at least one opening at a location proximal the distal section 32, away from the outlet end 33, to allow flow of aqueous in more than one direction. The at least one opening may be located on the distal section 32 at about opposite of the outlet end 33.

In another exemplary embodiment, the seton implant 31 may have a one-way flow controlling means 39 for allowing one-way aqueous flow 40. The one-way flow controlling means 39 may be selected from the group consisting of a check valve, a slit valve, a micropump, a semi-permeable membrane, or the like. To enhance the outflow efficiency, at least one optional opening 41 in the proximal portion of the distal section 32, at a location away from the outlet end 33, and in an exemplary embodiment at the opposite end of the outlet end 33, is provided.

Figure 4:
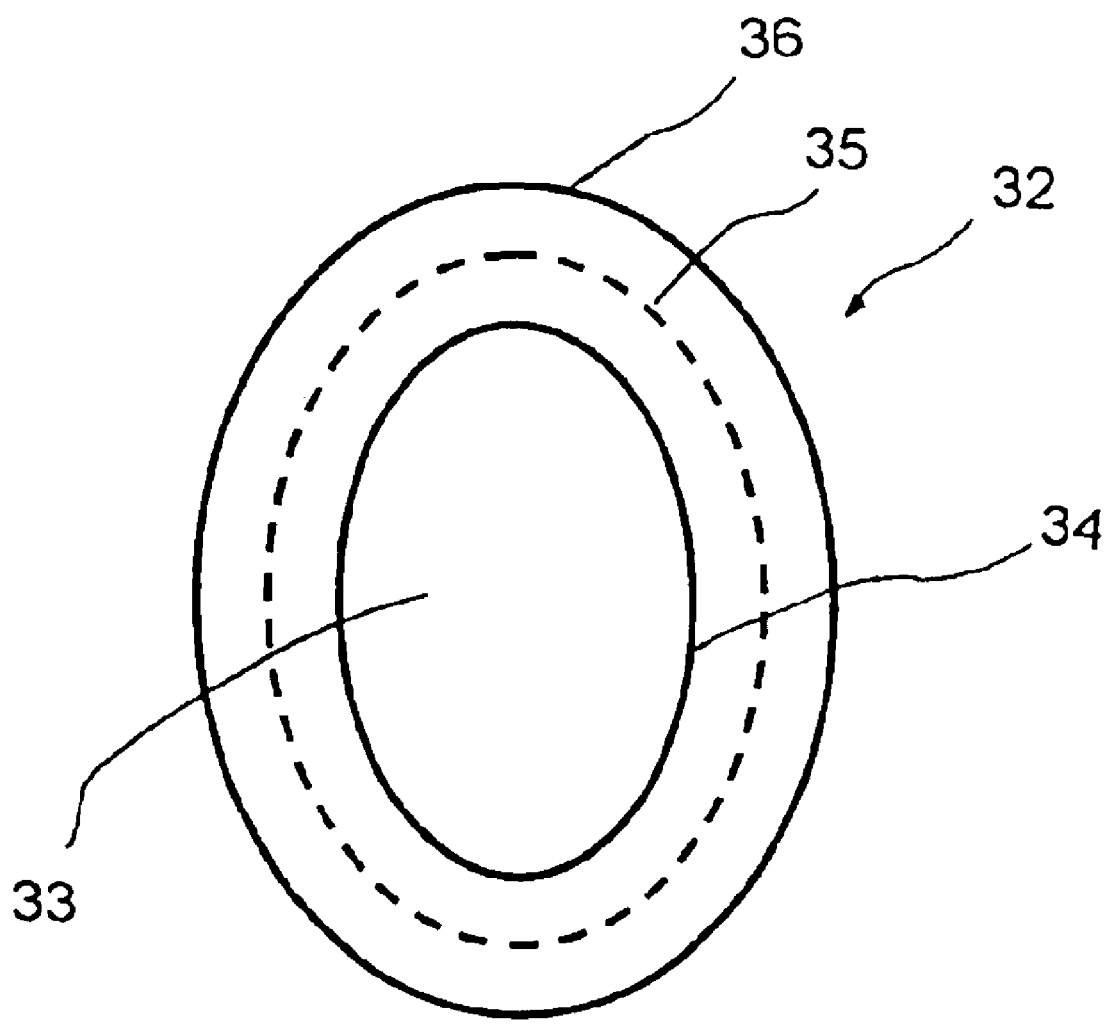
FIG. 4 is a top cross-sectional view of section 1—1 of FIG. 3.

FIG. 4 shows a top cross-sectional view of FIG. 3. The shape of the opening of the outlet end 33 and the remaining body of the distal section 32 may be oval, round or some other shape adapted to conform to the shape of the existing outflow pathways. This configuration will match the contour of Schlemm's canal to stabilize the inlet section with respect to the iris and cornea by preventing rotation.

As shown in FIG. 3, the seton implant of the present invention may have a length between about 0.5 mm to over a meter, depending on the body cavity the seton implant applies to. The outside diameter of the seton implant may range from about 30 μm to about 500 μm. The lumen diameter is preferably in the range between about 20 μm to about 150 μm. The seton implant may have a plurality of lumens to facilitate multiple flow transportation. The distal section may be curved at an angle between about 30 degrees to about 150 degrees, in an exemplary embodiment at around 70–110 degrees, with reference to the inlet section 44.

FIG. 5 shows another embodiment of the seton implant 45 constructed in accordance with the principles of the invention. In an exemplary embodiment, the seton implant 45 may comprise at least two sections: an inlet section 47 and an outlet section 46. The outlet section has an outlet opening 48 that is at the outlet end of the seton implant 45. The shape of the outlet opening 48 is preferably an oval shape to conform to the contour of the existing outflow pathways. A portion of the inlet section 47 adjacent the joint region to the outlet section 46 will be positioned essentially through the diseased trabecular meshwork while the remainder of the inlet section 47 and the outlet section 46 are outside the trabecular meshwork. As shown in FIG. 5, the long axis of the oval shape opening 48 lies in a first plane formed by an X-axis and a Y-axis. To better conform to the anatomical contour of the anterior chamber 20, the trabecular meshwork 21 and the existing outflow pathways, the inlet section 47 may preferably lie at an elevated second plane, at an angle θ, from the first plane formed by an imaginary inlet section 47A and the outlet section 46. The angle θ may be between about 30 degrees and about 150 degrees.

Figure 6:
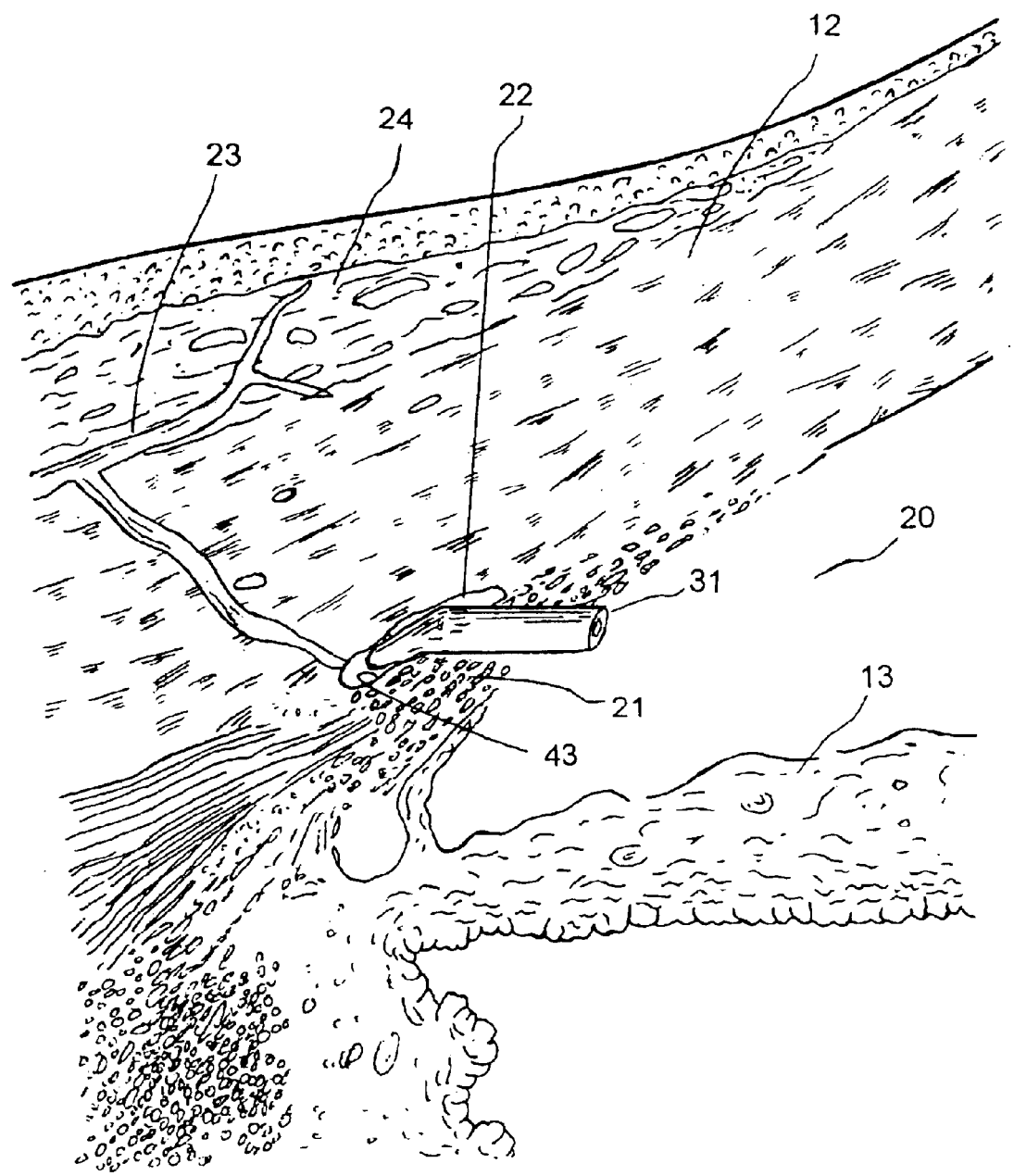
FIG. 6 is a perspective view illustrating the seton implant of the present invention positioned within the tissue of an eye.

FIG. 6 shows a perspective view illustrating the seton implant 31, 45 of the present invention positioned within the tissue of an eye 10. A hole/opening is created through the diseased trabecular meshwork 21. The distal section 32 of the seton implant 31 is inserted into the hole, wherein the inlet end 38 is exposed to the anterior chamber 20 while the outlet end 33 is positioned at about an exterior surface 43 of said diseased trabecular meshwork 21. In a further embodiment, the outlet end 33 may further enter into fluid collection channels of the existing outflow pathways.

In one embodiment, the means for forming a hole/opening in the trabecular mesh 21 may comprise an incision with a microknife, an incision by a pointed guidewire, a sharpened applicator, a screw shaped applicator, an irrigating applicator, or a barbed applicator. Alternatively, the trabecular meshwork may be dissected off with an instrument similar to a retinal pick or microcurrette. The opening may alternately be created by retrogade fiberoptic laser ablation.

Figure 7:
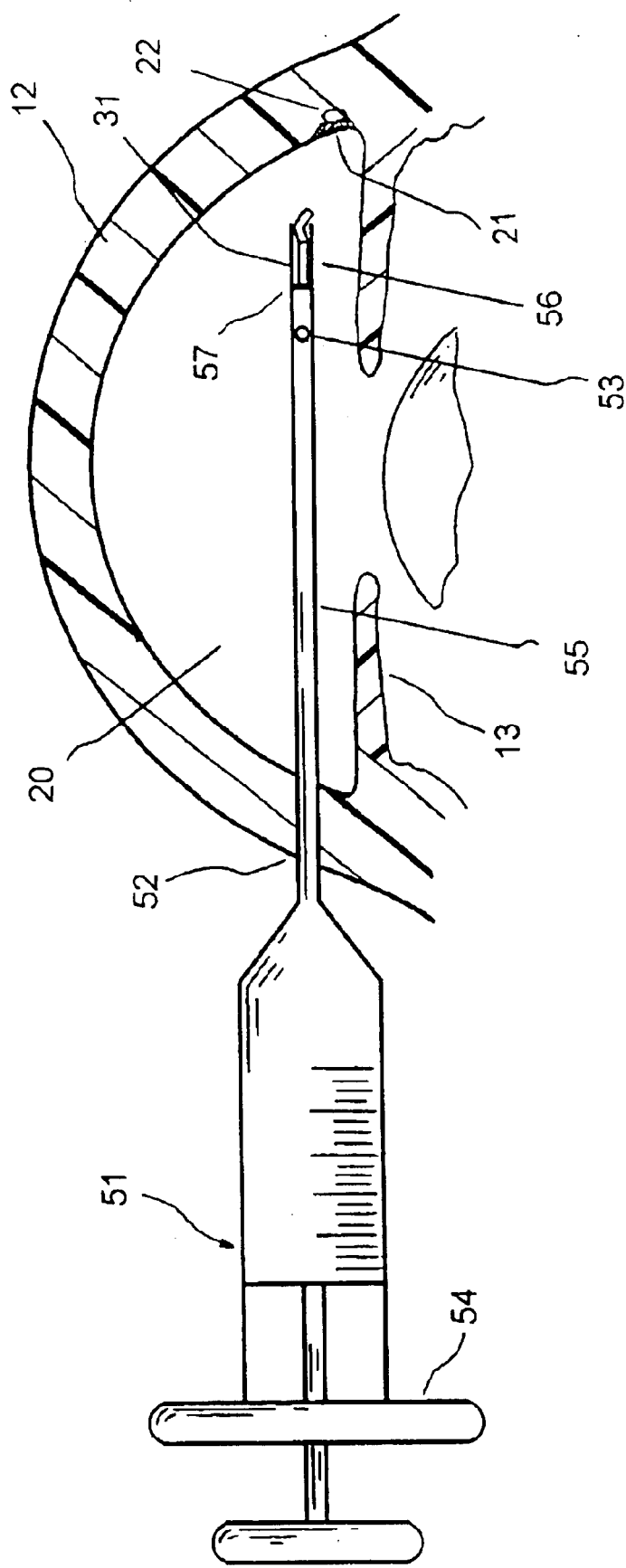
FIG. 7 is an alternate exemplary method for placing a seton implant at the implant site.

FIG. 7 shows an illustrative method for placing a seton implant at the implant site. An irrigating knife or applicator 51 comprises a syringe portion 54 and a cannula portion 55. The distal section of the cannula portion 55 has at least one irrigating hole 53 and a distal space 56 for holding a seton implant 31. The proximal end 57 of the lumen of the distal space 56 is sealed from the remaining lumen of the cannula portion 55.

For positioning the seton 31 in the hole or opening through the trabecular meshwork, the seton may be advanced over the guidewire or a fiberoptic (retrograde). In another embodiment, the seton is directly placed on the delivery applicator and advanced to the implant site, wherein the delivery applicator holds the seton securely during the delivery stage and releases it during the deployment stage.

In an exemplary embodiment of the trabecular meshwork surgery, the patient is placed in the supine position, prepped, draped and anesthesia obtained. In one embodiment, a small (less than 1 mm) self sealing incision is made. Through the cornea opposite the seton placement site, an incision is made in trabecular meshwork with an irrigating knife. The seton 31 is then advanced through the cornea incision 52 across the anterior chamber 20 held in an irrigating applicator 51 under gonioscopic (lens) or endoscopic guidance. The applicator is withdrawn and the surgery concluded. The irrigating knife may be within a size range of 20 to 40 gauges, preferably about 30 gauge.

From the foregoing description, it should now be appreciated that a novel approach for the surgical treatment of glaucoma has been disclosed for releasing excessive intraocular pressure. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. A device for treating glaucoma, comprising:
a substantially L-shaped body having an inlet portion and an outlet portion, said inlet portion configured to transport fluid from the anterior chamber to the outlet portion when the outlet portion is disposed in Schlemm's canal, said outlet portion having outflow openings disposed to deliver said fluid in opposite directions in Schlemm's canal.

2. The implant of claim 1, wherein the body comprises a tube.

3. The implant of claim 1, wherein the substantially L-shaped body comprises a tube.

4. The implant of claim 1, wherein the substantially L-shaped body has a lumen with an oval cross-section.

5. The implant of claim 1, wherein both of the outflow openings are in the L-shaped body.

6. An implant comprising a substantially L-shaped body having a first portion and a second portion, said implant configured to transport fluid from the anterior chamber of an eye to Schlemm's canal of the eye, when an end of the first portion is disposed in the anterior chamber and an end of the second portion is disposed in Schlemm's canal, said implant having outflow openings disposed to deliver said fluid in opposite directions in Schlemm's canal.

* * * * *

UNITED STATES PATENT AND TRADEMARK OFFICE
CERTIFICATE OF CORRECTION

PATENT NO. : 6,780,164 B2  Page 1 of 1
DATED : August 24, 2004
INVENTOR(S) : Bergheim et al.

It is certified that error appears in the above-identified patent and that said Letters Patent is hereby corrected as shown below:

<u>Title page,</u>
Item [56], References Cited, OTHER PUBLICATIONS,
"Phillip C. Jacobi, M.D.,..." reference, delete "Cronic" and insert -- Chronic --, thereof.

Signed and Sealed this

Twenty-ninth Day of November, 2005

JON W. DUDAS
*Director of the United States Patent and Trademark Office*